United States Patent
Nichols et al.

(10) Patent No.: US 10,252,860 B2
(45) Date of Patent: Apr. 9, 2019

(54) MODULAR SAMPLE STORAGE SYSTEM

(71) Applicant: HighRes Biosolutions, Inc., Woburn, MA (US)

(72) Inventors: Michael J. Nichols, Newburyport, MA (US); Louis J. Guarracina, Newburyport, MA (US)

(73) Assignee: HighRes Biosolutions, Inc., Beverly, MA (US)

( * ) Notice: Subject to any disclaimer, the term of this patent is extended or adjusted under 35 U.S.C. 154(b) by 660 days.

(21) Appl. No.: 14/593,522

(22) Filed: Jan. 9, 2015

(65) Prior Publication Data

US 2016/0200514 A1    Jul. 14, 2016

(51) Int. Cl.
*B65G 1/137* (2006.01)
*G01N 35/04* (2006.01)
*G01N 1/00* (2006.01)
*G01N 35/00* (2006.01)

(52) U.S. Cl.
CPC ............ *B65G 1/137* (2013.01); *G01N 35/04* (2013.01); *G01N 35/0099* (2013.01); *G01N 2001/002* (2013.01); *G01N 2035/00306* (2013.01); *G01N 2035/041* (2013.01); *G01N 2035/0406* (2013.01); *G01N 2035/0418* (2013.01); *G01N 2035/0425* (2013.01); *G01N 2035/0462* (2013.01); *G01N 2035/0465* (2013.01)

(58) Field of Classification Search
CPC .......................... G01N 2035/0451; B65G 1/137
See application file for complete search history.

(56) References Cited

U.S. PATENT DOCUMENTS

| | | | |
|---|---|---|---|
| 5,033,626 A | | 7/1991 | Platti |
| 5,885,529 A | * | 3/1999 | Babson ............... B01L 3/50853 134/150 |
| 5,885,530 A | * | 3/1999 | Babson ............... B01L 3/50853 422/63 |
| 6,206,493 B1 | | 3/2001 | Sanchez-Levin et al. |
| 7,115,384 B2 | | 10/2006 | Clark et al. |
| 7,270,784 B2 | | 9/2007 | Vuong et al. |

(Continued)

FOREIGN PATENT DOCUMENTS

DE      102004053170 A1    5/2006
DE      202013104657 U1    12/2013
(Continued)

OTHER PUBLICATIONS

EP Search Report for EP Application No. 16150564.9, dated Jun. 14, 2016.

*Primary Examiner* — Jonathan Snelting
(74) *Attorney, Agent, or Firm* — Perman & Green, LLP

(57) ABSTRACT

Various embodiments include a sample storage system having: a transport module; a storage module coupled with the transport module on at least one side of the transport module, the storage module for storing a plurality of specimen tubes or microtiter plates; a tube selector module coupled to an end of the transport module for selecting at least one of the plurality of specimen tubes or microtiter plates; and an input/output (I/O) module coupled with the transport module on a side of the transport module, wherein the transport module is configured to modularly couple with at least one additional storage module for storing a plurality of specimen tubes or microtiter plates.

18 Claims, 10 Drawing Sheets

(56) References Cited

U.S. PATENT DOCUMENTS

| | | |
|---|---|---|
| 7,390,458 B2 | 6/2008 | Burow et al. |
| 7,513,127 B2 * | 4/2009 | Owen ................ A01N 1/02 |
| | | 422/65 |
| 8,252,232 B2 * | 8/2012 | Neeper ............ G01N 35/00732 |
| | | 198/468.8 |
| 8,554,362 B2 | 10/2013 | Raghibizadeh et al. |
| 8,580,195 B2 | 11/2013 | Frey et al. |
| 8,728,413 B2 | 5/2014 | Talmer et al. |
| 2003/0215357 A1 | 11/2003 | Malterer et al. |
| 2004/0037680 A1 | 2/2004 | Sato et al. |
| 2004/0213651 A1 | 10/2004 | Malin |
| 2006/0018791 A1 | 1/2006 | Riling et al. |
| 2008/0011697 A1 | 1/2008 | Berg |
| 2008/0056957 A1 | 3/2008 | Hayman |
| 2008/0131961 A1 | 6/2008 | Crees et al. |
| 2008/0231157 A1 | 9/2008 | Lowe |
| 2009/0023128 A1 | 1/2009 | Zimmermann et al. |
| 2012/0060539 A1 | 3/2012 | Hunt et al. |
| 2012/0283867 A1 | 11/2012 | Gelbman et al. |
| 2013/0011226 A1 | 1/2013 | Camenisch et al. |
| 2013/0255283 A1 | 10/2013 | Berchowitz |
| 2014/0025199 A1 | 1/2014 | Berg et al. |

FOREIGN PATENT DOCUMENTS

| | | |
|---|---|---|
| EP | 1939561 A2 | 7/2008 |
| EP | 2068105 A2 | 6/2009 |
| JP | H0719717 A | 1/1995 |
| JP | 2002129503 A | 5/2002 |
| JP | 2005083777 A | 3/2005 |
| JP | 2010210546 A | 9/2010 |
| WO | 0008473 A1 | 2/2000 |
| WO | 2011048058 A1 | 4/2011 |
| WO | 2011108988 A1 | 9/2011 |
| WO | 2013149117 A2 | 10/2013 |

* cited by examiner

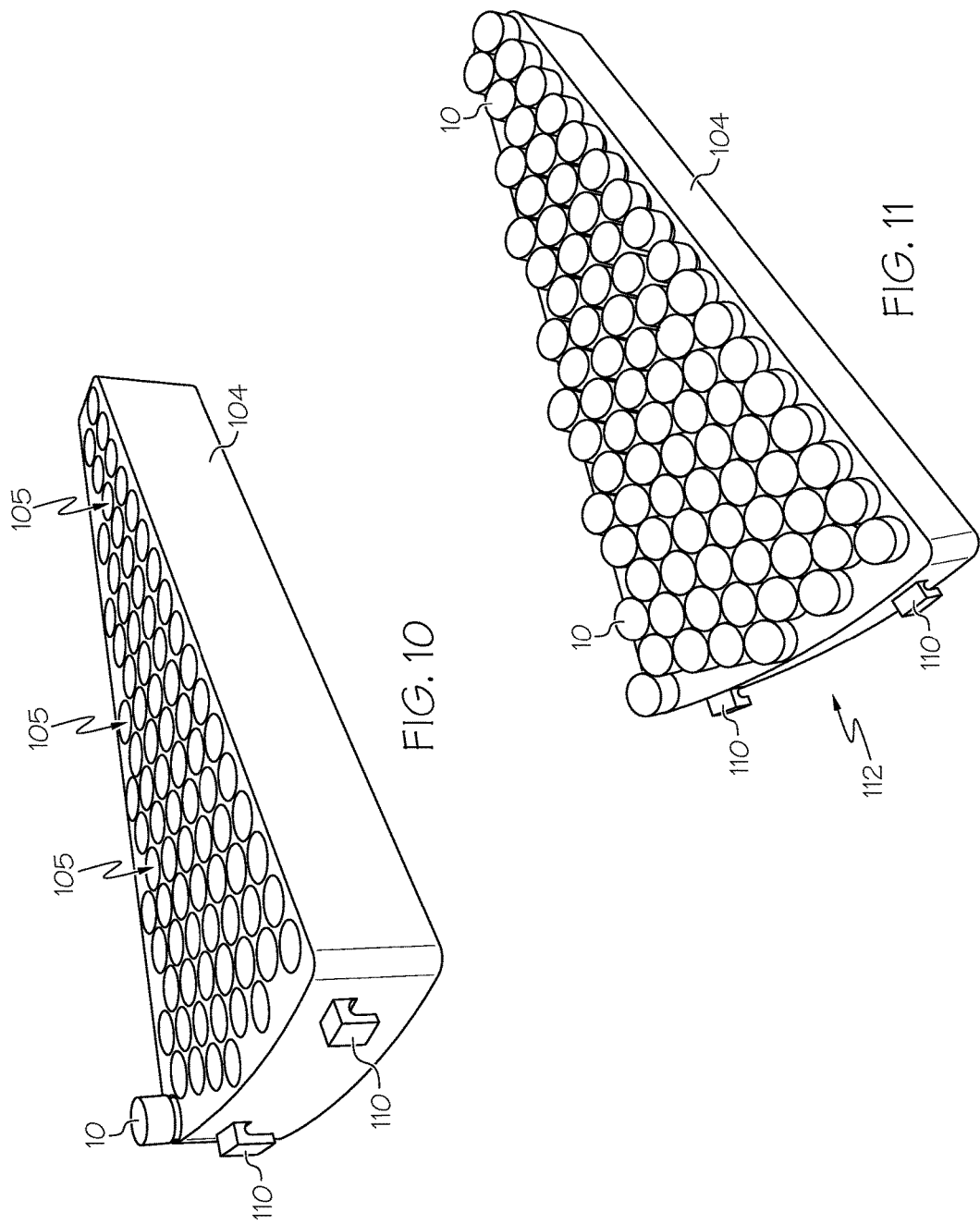

MODULAR SAMPLE STORAGE SYSTEM

FIELD

The subject matter disclosed herein relates to life sciences equipment. More particularly, the subject matter disclosed herein relates to sample storage equipment for use in the life sciences industry.

BACKGROUND

Sample storage units are laboratory tools commonly used in the life sciences industry to store biological or chemical samples. Sample storage units take many shapes and sizes. However, many conventional sample storage units are stand-alone compartments, which have limited accessibility and flexibility in allowing for additional storage and/or transporting samples.

BRIEF DESCRIPTION

Various embodiments include a sample storage system having: a transport module; a storage module coupled with the transport module on at least one side of the transport module, the storage module for storing a plurality of specimen tubes or microtitre plates; a tube selector module coupled to an end of the transport module for selecting at least one of the plurality of specimen tubes or microtitre plate; and an input/output (I/O) module coupled with the transport module on a side of the transport module, wherein the transport module is configured to modularly couple with at least one additional storage module for storing a plurality of specimen tubes or microtitre plates.

A first aspect includes a sample storage system having: a transport module; a storage module coupled with the transport module on at least one side of the transport module, the storage module for storing a plurality of specimen tubes or microtitre plates; a tube selector module coupled to an end of the transport module for selecting at least one of the plurality of specimen tubes or microtitre plates; and an input/output (I/O) module coupled with the transport module on a side of the transport module, wherein the transport module is configured to modularly couple with at least one additional storage module for storing a plurality of specimen tubes or microtitre plates.

A second aspect includes a sample storage system having: a transport module; a storage module coupled with the transport module on at least one side of the transport module, the storage module for storing a plurality of specimen tubes or microtitre plates; a tube selector module coupled to an end of the transport module for selecting at least one of the plurality of specimen tubes or microtitre plates; and an input/output (I/O) module coupled with the transport module on a side of the transport module, the I/O module for at least one of inputting or outputting at least one of the plurality of specimen tubes or microtitre plates from the storage module via the transport module, wherein the transport module is configured to modularly couple with at least one additional storage module for storing a plurality of specimen tubes or microtitre plates.

A third aspect includes a sample storage system including: a transport module having a transport rail system; a plurality of storage modules coupled with the transport module on at least one side of the transport module, each of the plurality of storage modules for storing a plurality of specimen tubes or microtitre plates; a tube selector module coupled to an end of the transport module distinct from the at least one side, the tube selector module for selecting at least one of the plurality of specimen tubes or microtitre plates from the transport rail system; and an input/output (I/O) module coupled with the transport module on a side of the transport module, the I/O module for at least one of inputting or outputting at least one of the plurality of specimen tubes or microtitre plates from the storage module via the transport module, wherein the transport module is configured to modularly couple with at least one additional storage module for storing a plurality of specimen tubes or microtitre plates.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which:

FIGS. 10-11 show three-dimensional perspective views of a wedge-shaped vial storage module from the storage rack of FIG. 9, according to various embodiments.

Figure 1:
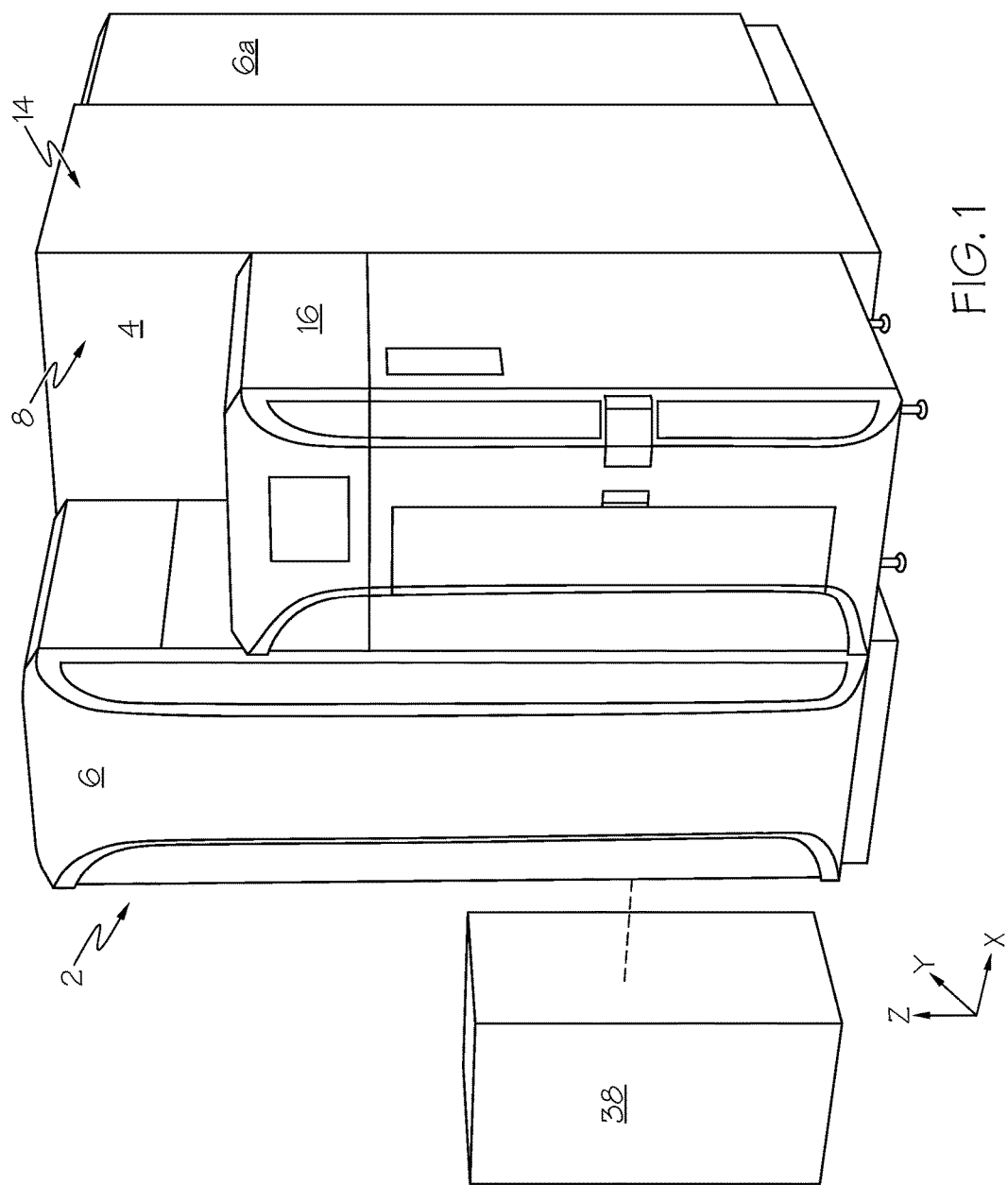
FIG. 1 shows a side perspective view of a system according to various embodiments.

It is noted that the drawings of the invention are not necessarily to scale. The drawings are intended to depict only typical aspects of the invention, and therefore should not be considered as limiting the scope of the invention. In the drawings, like numbering represents like elements between the drawings.

DETAILED DESCRIPTION

As indicated above, the subject matter disclosed herein relates to life sciences equipment. More particularly, the subject matter disclosed herein relates to pipetting equipment for use in the life sciences industry.

As noted herein, sample storage units are laboratory tools commonly used in the life sciences industry to store biological or chemical samples. Sample storage units take many shapes and sizes, but many conventional sample storage units are stand-alone compartments, which have limited accessibility and flexibility in allowing for additional storage and/or transporting samples.

In contrast to conventional sample storage systems, various embodiments include a modular sample storage system, allowing for adjustment of at least one of: a number of storage modules, a number and/or length of transport modules, a number of tube selectors, or a number and/or format of input/output (I/O) modules. The modular sample storage system can include a set of storage modules positioned around a central transport module, a tube selector module and an input/output (I/O) module. The transport module is referred to herein in some embodiments as being a "central" transport module, merely to denote its relationship with the other modules in the sample storage systems described. That is, the transport module, according to various embodiments, is located between the storage module, tube selector module and/or I/O module, each of which is described herein in further detail.

In the following description, reference is made to the accompanying drawings that form a part thereof, and in which is shown by way of illustration specific example embodiments in which the present teachings may be practiced. These embodiments are described in sufficient detail to enable those skilled in the art to practice the present teachings and it is to be understood that other embodiments may be utilized and that changes may be made without departing from the scope of the present teachings. The following description is, therefore, merely exemplary.

FIG. 1 shows a three-dimensional perspective view of a sample storage system (or simply, system) 2 according to various embodiments. As shown, the sample storage system 2 can include a (central) transport module 4, and at least one storage module 6 coupled with the (central) transport module 4 on at least one side 8 of the (central) transport module 4. As described herein, the storage module(s) 6 can be modularly (or, detachably) coupled with the (central) transport module 4, such that one or more storage module(s) 6 can be added or subtracted from the sample storage system 2 within approximately one hour. The storage module(s) 6 can be configured to store a plurality of specimen tubes (or in some embodiments, microtitre plates) 10 (FIG. 4), which may include or be designed to contain life sciences specimens (e.g., biological, chemical, or similar samples). The transport module 4 is referred to herein in some embodiments as being a "central" transport module 4, merely to denote its relationship with the other modules in the sample storage systems described. That is, the transport module 4, according to various embodiments, is located between the storage module, tube selector module and/or I/O module, each of which is described herein in further detail. As described herein, the position of the transport module 4 relative to the other modules may provide various benefits in use of the sample storage system 2.

Various components are labeled in FIGS. 1-8 which are shown and described in greater detail according to additional FIGURES. It is understood that multiple figures are referenced for clarity of illustration and explanation.

Figure 6:
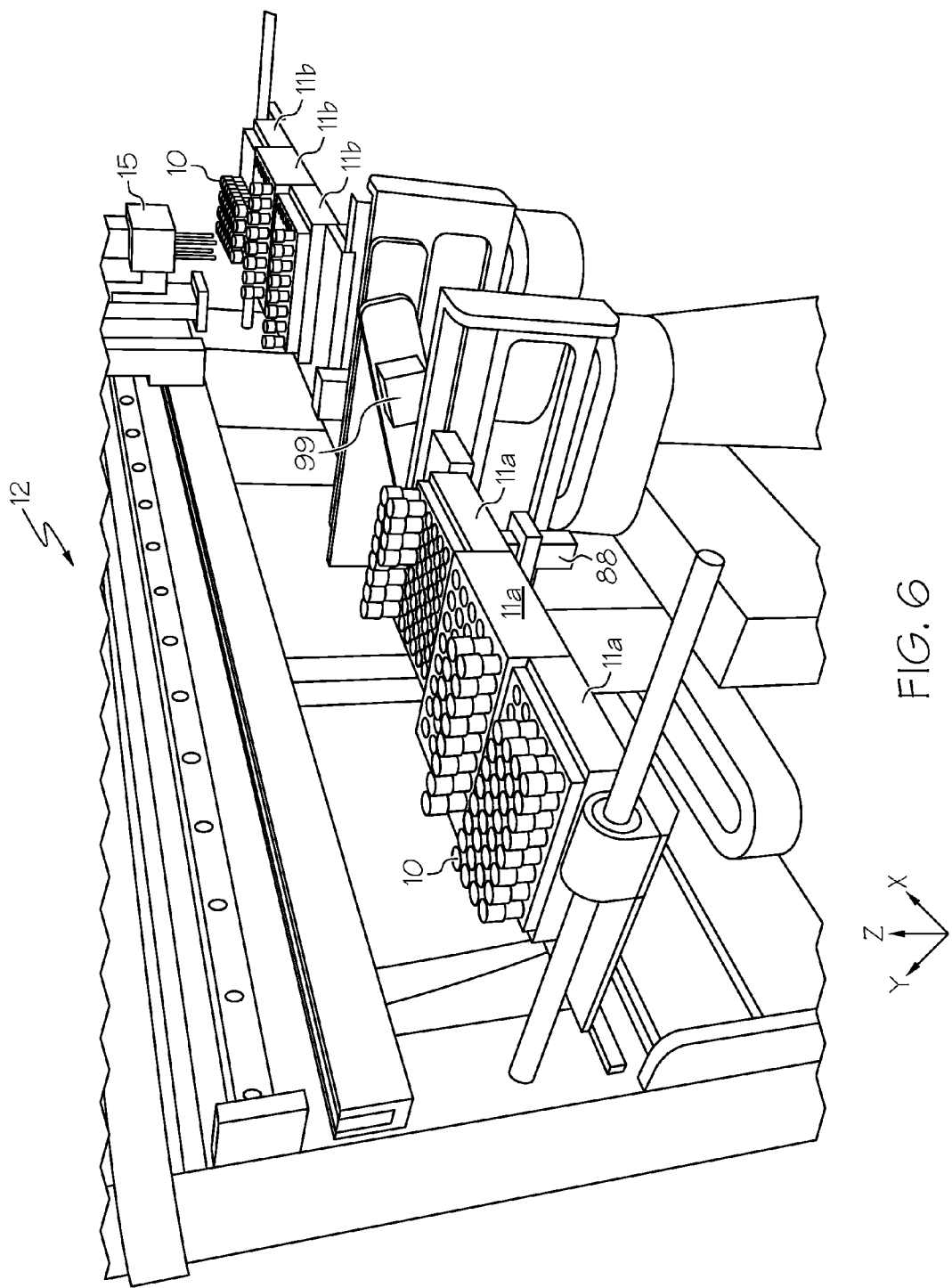
FIG. 6. shows a close-up perspective view of a portion of a tube selector module according to various embodiments
Figure 7:
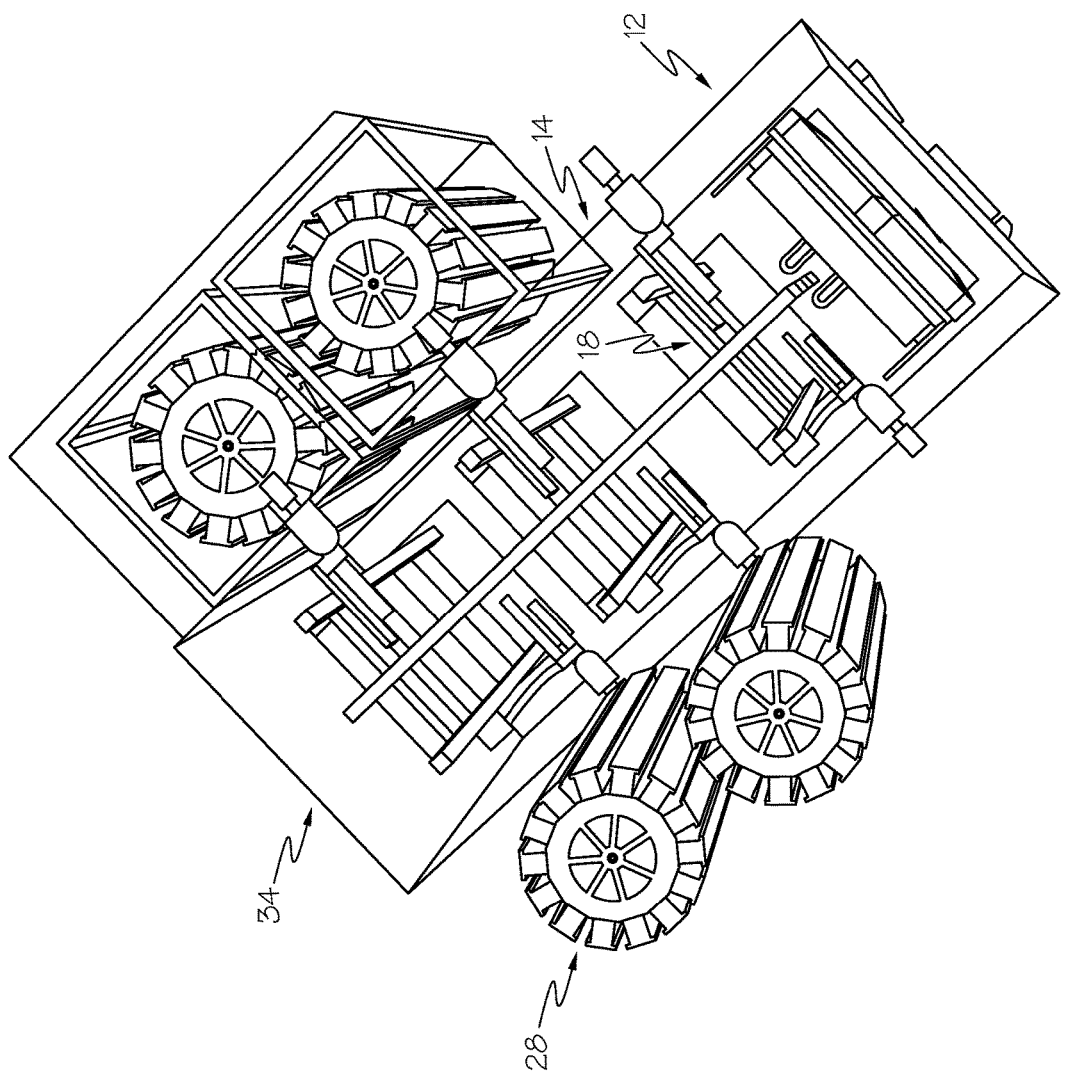
FIG. 7 shows a top-down cut-away perspective view of the system of FIG. 1.

The system 2 can further include a tube selector module 12, shown most clearly in the cut-away three-dimensional perspective views of FIGS. 2, 3, 6 and 7. The tube selector module 12 is coupled to an end 14 of the central transport module 4, where the tube selector module 12 is configured to select at least one of the plurality of specimen tubes or microtitre plates 10. In various embodiments, the tube selector module 14 can include a plurality of tube selectors 15 (FIG. 6). According to various embodiments, with particular reference to FIG. 6, two independent trays 11a and 11b are configured to receive both source and destination tube racks. Tube selector(s) 15 can include a two jaw or four-jaw gripper actuator mounted on a gantry (e.g., an x-y gantry or an x-y-z gantry). In some cases, in order to transfer a tube from a source tray (e.g., tray 11a) to a destination tray (e.g., tray 11b), tube selector 15 can move along the x-direction (x) while tray 11a simultaneously moves along the y-direction (y), via a sliding transport mechanism 99, such that the selector 15 is located directly above (in z-direction) the specimen tube/microtitre plate 10 being selected. In various embodiments, the sliding transport mechanism 99 can include, for example, a track system with set of bearings, and a central sliding member located within the track. The central sliding member can move along the set of bearings, and transport the tray 11a. In various embodiments, the sliding transport mechanism 99 includes a motorized component to control movement of the tray 11a via the central sliding member. In various embodiments, the selector 15 can have a set of jaws, which can be opened, and subsequently or at a substantially same time, the selector 15 moves down in the z-direction (z) and the gripper closes on the desired specimen tube (microtitre plate) 10. In this case, the tube selector 15 may move upward in the z-direction, and subsequently, in the x-direction, while tray 11b moves in the y-direction in order to position the selector 15 (e.g., gripper) above the corresponding position in the destination rack. The selector 15 may then move downward in the z-direction and release the specimen tube 10. In cases where specimen tubes 10 are tightly packed, such that it would be difficult for gripper fingers of a selector 15 to insert into the interstices of the tubes 10, a tube lifter 88 may be employed, and may sit below trays 11 and track (follow) the x-directional movement of selector 15. In various embodiments, the tube lifter 88 can include a mechanically and/or pneumatically actuateable flange, that can move along the z-axis to contact an underside of a desired tube 10, and displace the desired tube 10 upward (in the z-direction). The tube lifter 88 can be electrically controlled via conventional control system software, described herein. In these embodiments, rather than selector 15 lowering its gripper below the plane defined by the top of the tubes 10, lifter 88 can engage an underside of a desired tube 10, and move the desired tube 10 upward in the z-direction (above the plane defined by the top of tubes 10. In these cases, the selector (gripper) 15 can open to grasp the selected tube 10.

Figure 2:
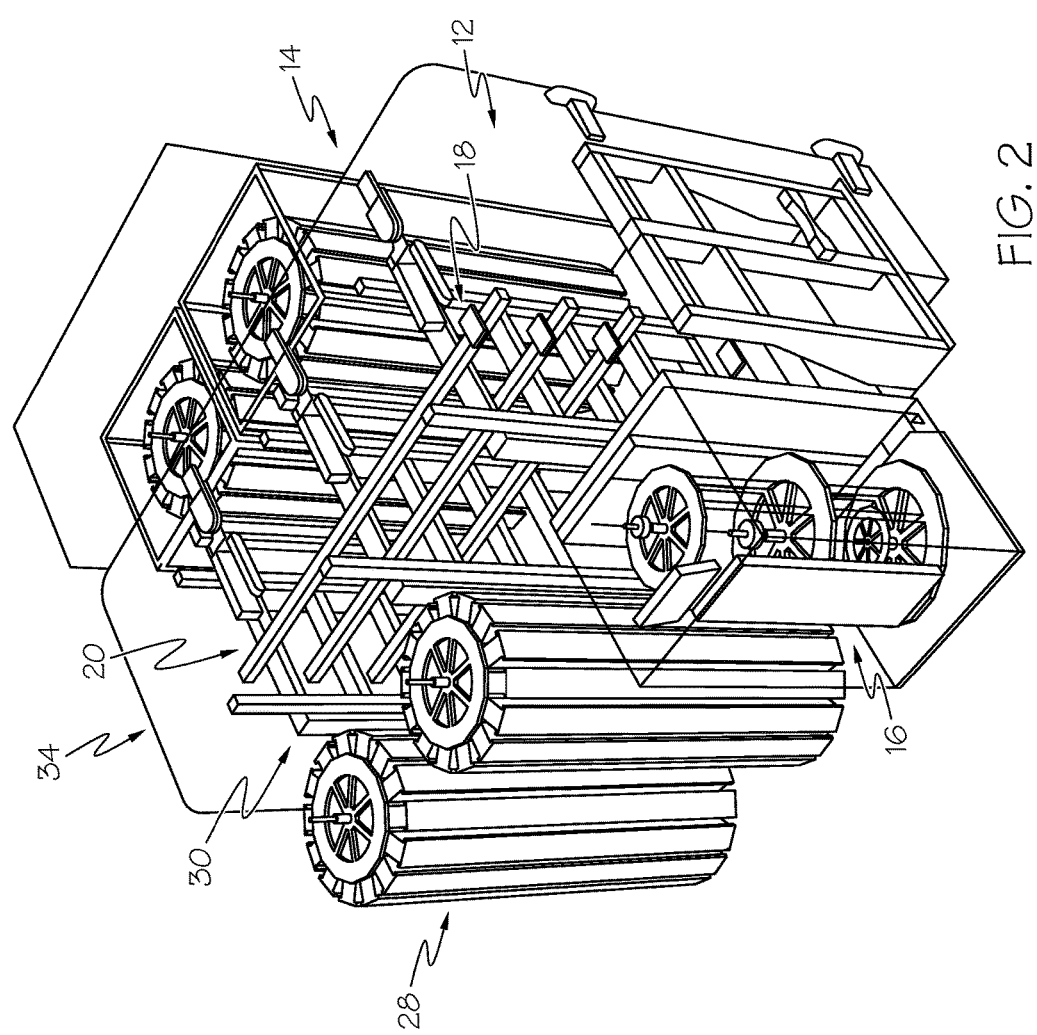
FIG. 2 and FIG. 3 show distinct cut-away perspective views of the system of FIG. 1.
Figure 3:
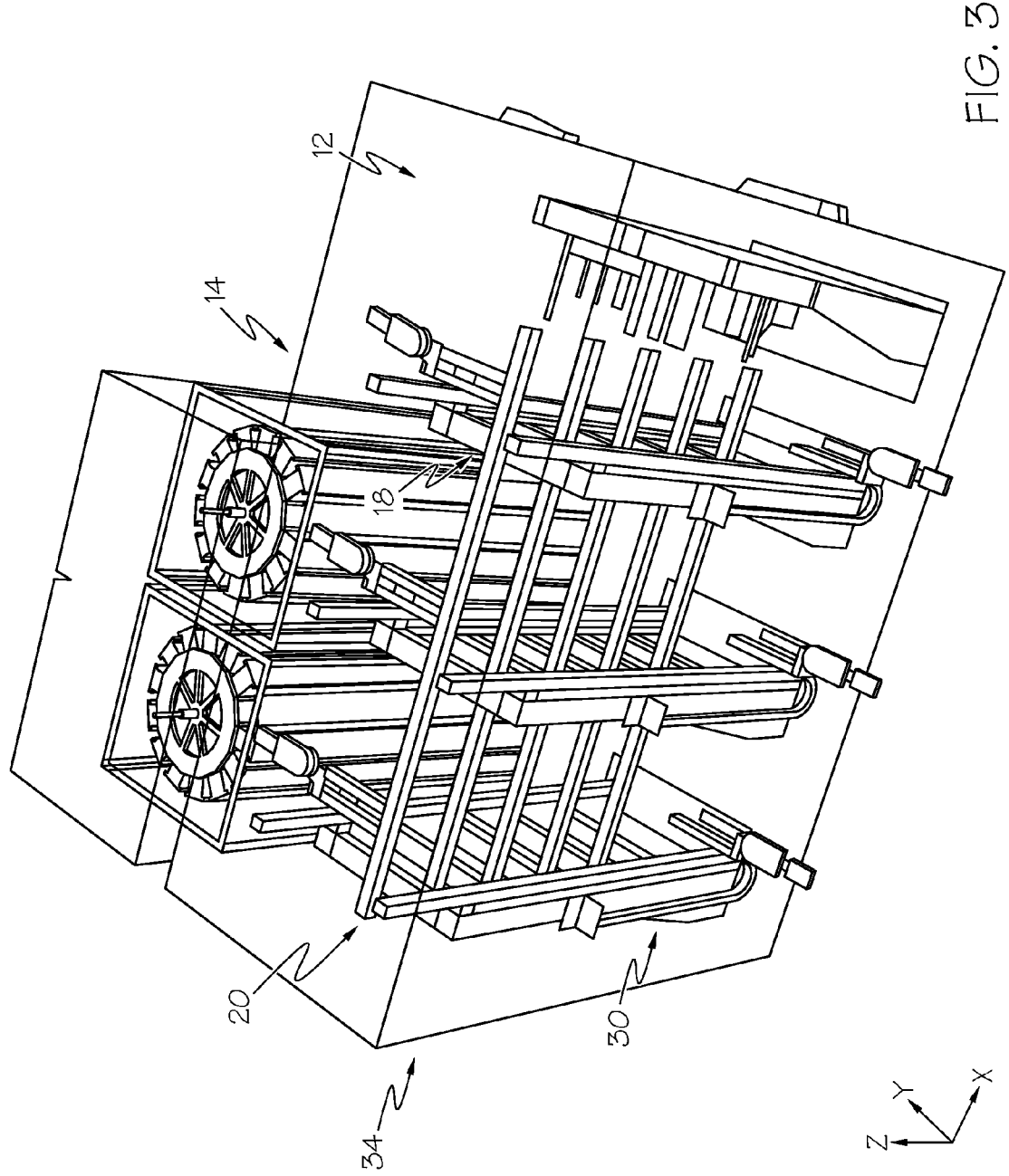

Referring to FIGS. 1-3, the system 2 can further include an input/output (I/O) module 16 coupled with the central transport module 4 on a side 8 of the central transport module 4. It is understood that according to some embodiments, the I/O module 16 is coupled with the central transport module 4 on a same side 8 as storage module(s) 6, but in some cases, the I/O module 16 is coupled to the central transport module 4 on a distinct side from at least one of the storage modules 6. In various embodiments, the I/O module 16 is configured to modularly attach and modularly detach from the central transport module 4, on demand. In various embodiments, the I/O module 16 further includes a storage rack 28 for storing specimen tubes (or microtitre plates) 10 during transport to/from an external system 26 (FIG. 8), such as an incubator system, centrifuge system, or other system used in the life sciences industry.

As shown and described herein, the central transport module 4 is configured to modularly couple with at least one additional storage module 6a (substantially similar to storage module 6), as shown in FIG. 1. That is, the central transport module 4 can be modularly coupled with various other modules to allow for dynamic expansion and/or contraction of the storage capacity of the system 2. As shown, the central transport module 4 can include an access aperture 18 (FIGS. 2-3) at the end 14 of the central transport module 4. The access aperture 18 allows the tube selector module 12 to access the transport system 20 (e.g., rail system 22) in the central transport module 14.

Figure 4:
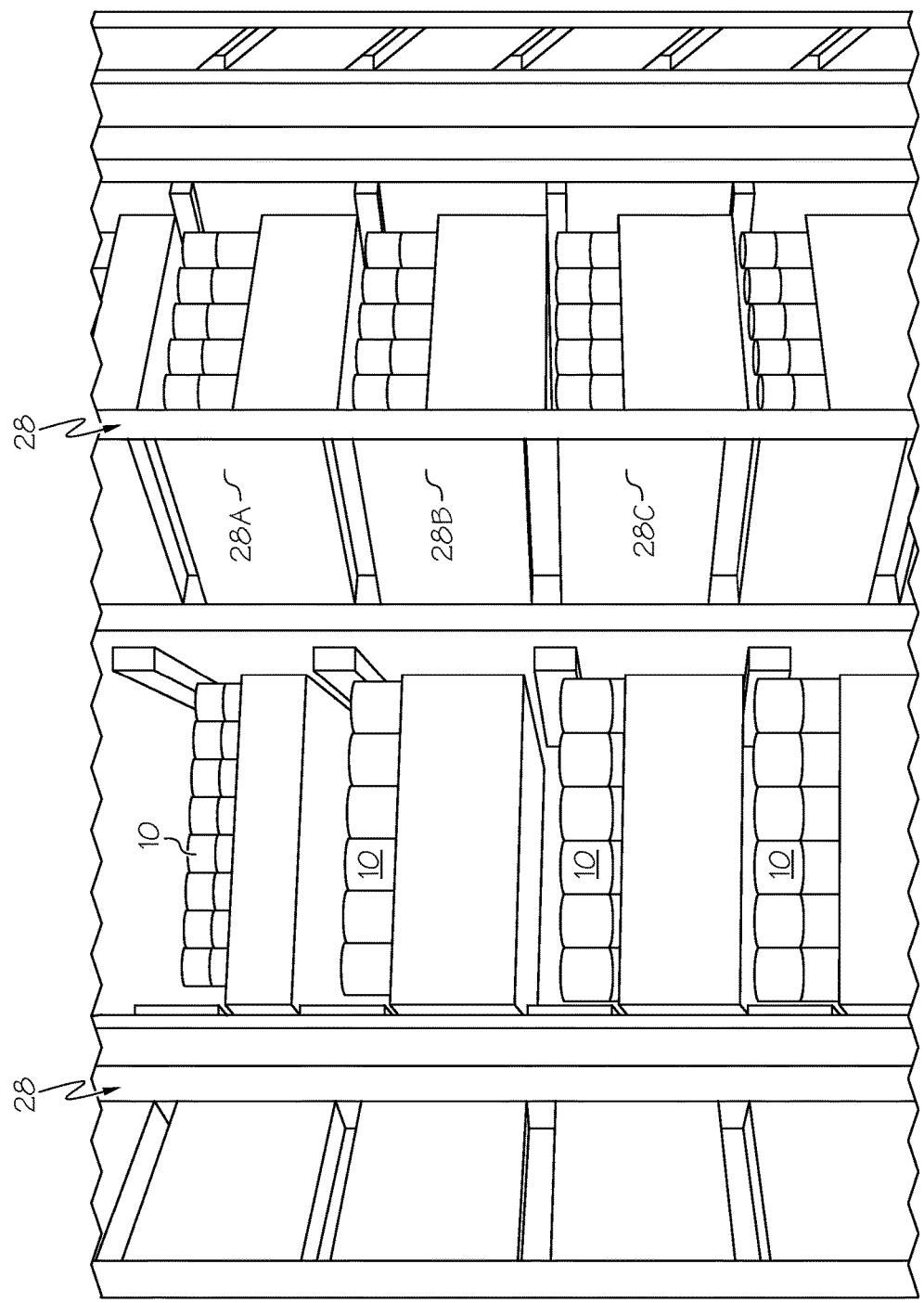
FIG. 4 shows a close-up three-dimensional view of a portion of a storage module according to various embodiments.
Figure 5:
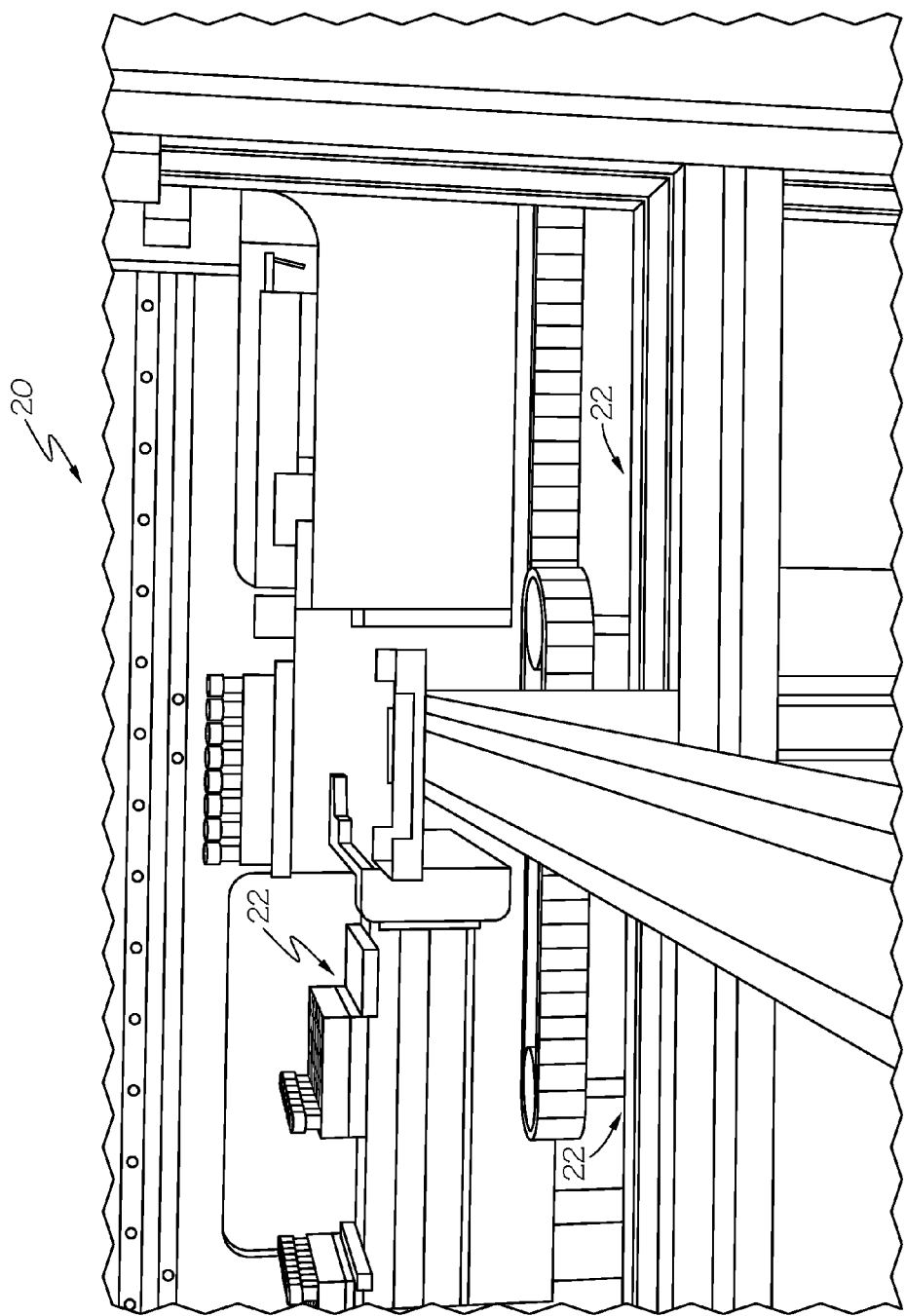
FIG. 5 shows a close-up perspective view of a portion of a (central) transport module according to various embodiments.

The storage module 6 can, in some embodiments, include a multi-level storage rack 28. FIG. 4 shows a close-up perspective view of a section of the multi-level storage rack 28 according to various embodiments. The storage module 6 can house tube racks or plates in at least two different configurations. In a first configuration, the storage racks 28 are arranged in a circular pattern in a rotating carousel (e.g., as seen in FIG. 2 and FIG. 3). A plate/rack selector in the central transport module 4 can select the desired plate or rack from its corresponding storage position in the column of positions presented by the storage rack 28 carousel. Selecting from only one column allows for a relatively small opening between storage module 6 and central transport module 4. In a second configuration, the storage module can be arranged in a static Cartesian x-y pattern. The plate/rack selector in central transport module 4 can select the desired plate or rack from the corresponding storage position in any column of positions across the entire width of the storage module 6. This configuration may require a wider opening between storage module 6 and central transport module 4. A larger opening may also require a larger door in order to seal off the environment in the storage module 6 environment from that of the central transport module 4. In addition, in this second configuration, the central transport module 4 is deeper than the trays/racks it is removing from the storage module 6. In contrast to the second configuration, the carousel design in the first configuration can allow for the use of a deeper storage module 6 while presenting smaller trays/racks to the central transport module 4, which allows the central transport module 4 to be comparatively compact.

Turning to FIGS. 3-4, according to various embodiments, the central transport module 4 includes a multi-level transport system 30 that is configured to transport at least one of the plurality of specimen tubes/microtitre plates 10 between distinct levels 28A, 28B, 28C, etc. in the multi-level storage rack 28. In various embodiments, the central transport module 14 includes a service door 34 providing access to the central transport module 14, e.g., for service. In various embodiments, as described herein, the central transport module 14 can be configured to move each specimen tube/microtitre plates 10 in three directions, (Z-direction, perpendicular to both the X-direction and Y-direction).

Referring again to FIG. 1, according to various embodiments, the system 2 can further include a control system (CS) 38, coupled to at least one of the central transport module 4, storage module(s) 6 and/or I/O module 16. As described herein, the control system (CS) 38 can include any conventional control system components used in controlling laboratory equipment (including, e.g., central transport module 4 storage module(s) 6 and/or I/O module 16). For example, the control system 38 can include electrical and/or electro-mechanical components for actuating one or more components in the central transport module 4, storage module(s) 6 and/or I/O module 16. The control system 38 can include conventional computerized sub-components such as a processor, memory, input/output, bus, etc. The control system 38 can be configured (e.g., programmed) to perform functions based upon operating conditions from an external source (e.g., at least one computing device), and/or may include pre-programmed (encoded) instructions based upon parameters of the central transport module 4, storage module(s) 6 and/or I/O module 16.

In various embodiments, the control system 38 is embodied, e.g., stored and/or operated in at least one computing device, which is connected (e.g., wirelessly and/or via hard-wiring) with the central transport module 4, storage module(s) 6 and/or I/O module 16. One or more of the processes described herein can be performed, e.g., by at least one computing device, such as control system 38, as described herein. In other cases, one or more of these processes can be performed according to a computer-implemented method. In still other embodiments, one or more of these processes can be performed by executing computer program code (e.g., control system 38) on at least one computing device, causing the at least one computing device to perform a process, e.g., controlling operation of central transport module 4, storage module(s) 6 and/or I/O module 16.

In any event, control system 38 (e.g., at least one computing device) can comprise one or more general purpose computing articles of manufacture (e.g., computing devices) capable of executing program code installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, control system 38 can be embodied as any combination of system software and/or application software. In any event, the technical effect of control system 8 is to control operation of central transport module 4, storage module(s) 6 and/or I/O module 16.

Further, control system 38 can be implemented using a set of modules In this case, a module can enable control system 38 to perform a set of tasks used by control system 38, and can be separately developed and/or implemented apart from other portions of control system 38. Control system 38 may include modules which comprise a specific use machine/hardware and/or software. Regardless, it is understood that two or more modules, and/or systems may share some/all of their respective hardware and/or software. Further, it is understood that some of the functionality discussed herein may not be implemented or additional functionality may be included as part of control system 38.

When control system 38 comprises multiple computing devices, each computing device may have only a portion of control system 38 embodied thereon (e.g., one or more modules). However, it is understood that control system 38 (and its computing device(s)) are only representative of various possible equivalent computer systems that may perform a process described herein. To this extent, in other embodiments, the functionality provided by computing device and control system 8 can be at least partially implemented by one or more computing devices that include any combination of general and/or specific purpose hardware with or without program code. In each embodiment, the hardware and program code, if included, can be created using standard engineering and programming techniques, respectively.

Regardless, when control system 38 includes multiple computing devices, the computing devices can communicate over any type of communications link. Further, while performing a process described herein, control system 38 can communicate with one or more other computer systems using any type of communications link. In either case, the communications link can comprise any combination of various types of wired and/or wireless links; comprise any combination of one or more types of networks; and/or utilize any combination of various types of transmission techniques and protocols.

As discussed herein, control system 38 enables control of central transport module 4, storage module(s) 6 and/or I/O module 16. Control system 38 may include logic for performing one or more actions described herein. In one embodiment, control system 38 may include logic to perform the above-stated functions. Structurally, the logic may take any of a variety of forms such as a field programmable gate array (FPGA), a microprocessor, a digital signal processor, an application specific integrated circuit (ASIC) or any other specific use machine structure capable of carrying out the functions described herein. Logic may take any of a variety of forms, such as software and/or hardware. However, for illustrative purposes, control system 38 and logic included therein will be described herein as a specific use machine. As will be understood from the description, while logic is illustrated as including each of the above-stated functions, not all of the functions are necessary according to the teachings of the invention as recited in the appended claims.

Figure 8:
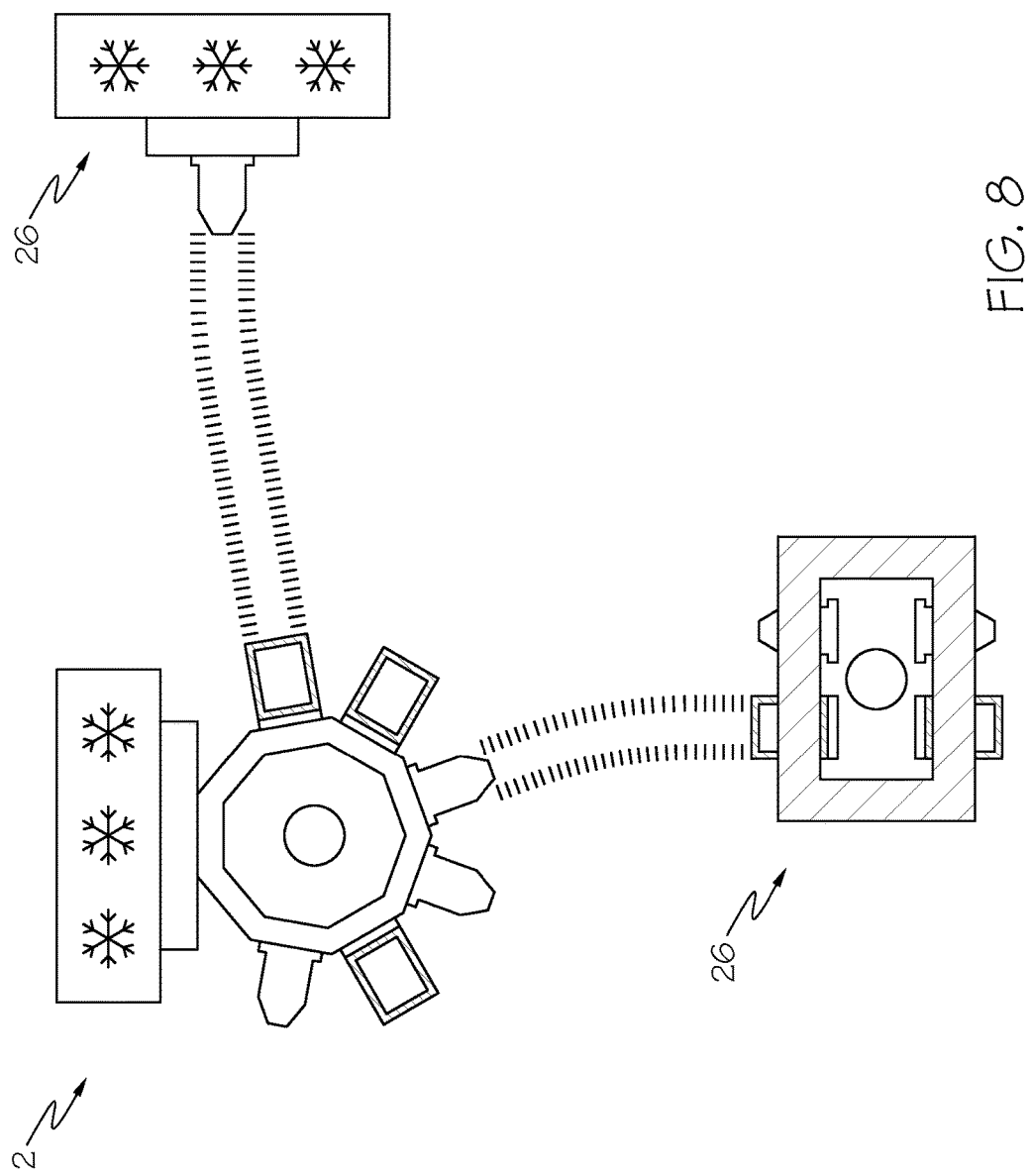
FIG. 8 shows a top schematic view of an environment including the system of FIG. 1.

FIG. 8 shows an environment 40 including a configuration of the modular system 2 shown and described with reference to FIGS. 1-7. As shown, the system 2 can interact with external systems 26 as described herein, for example to transport, test, store, etc. life sciences samples.

Figure 9:
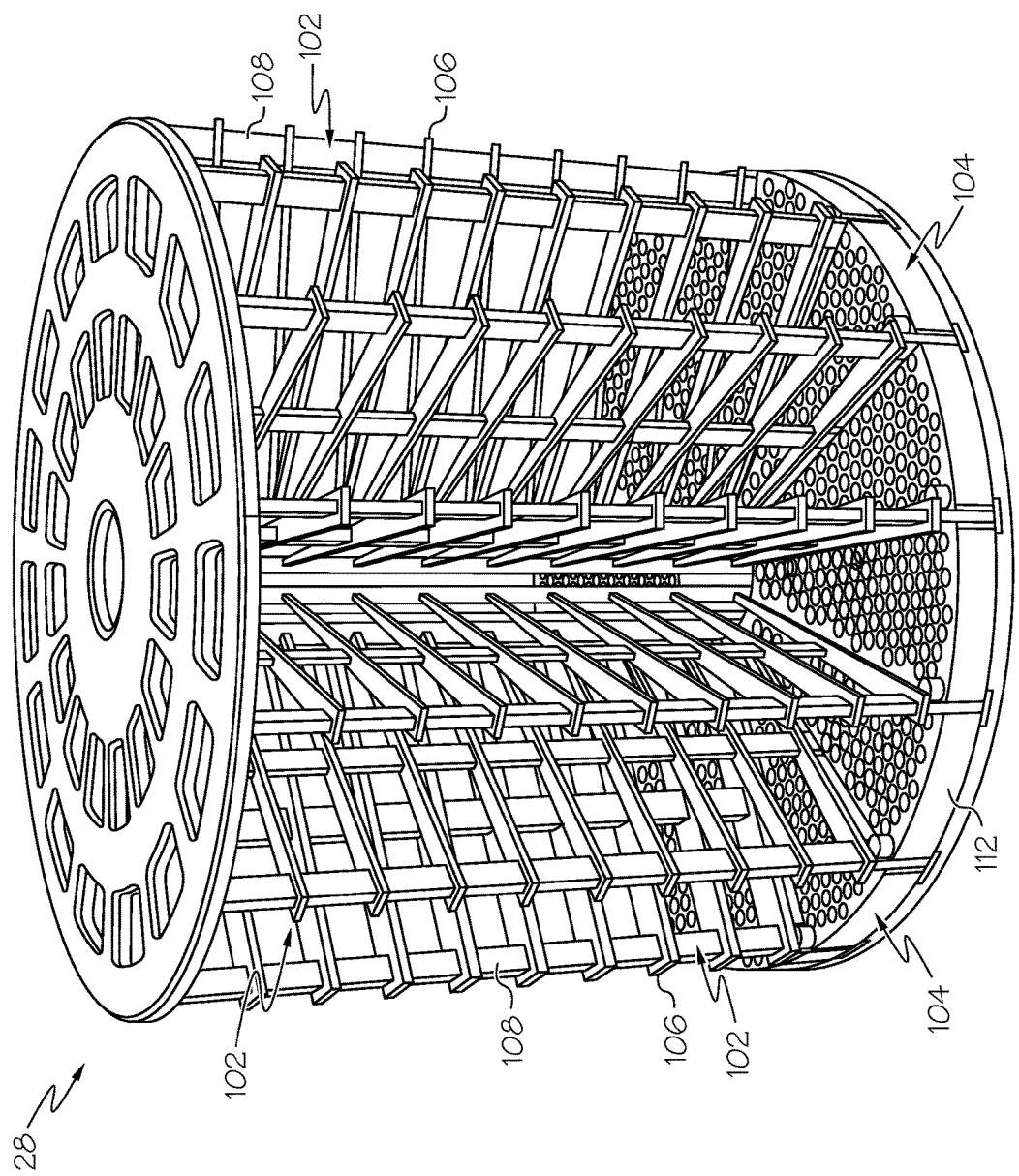
FIG. 9 shows a three-dimensional perspective view of a section of a storage rack according to various embodiments.

FIG. 9 shows a three-dimensional perspective view of a section of a storage rack 28 (e.g., as shown in FIG. 1) according to various embodiments. As shown, the storage rack 28 can include a plurality of wedge-shaped compartments 102, each for holding a wedge-shaped vial storage module 104. The wedge-shaped compartments 102 can include a set of vertically aligned support members 106, extending partially circumferentially from a set of vertical columns 108. The support members 106 can provide vertical support for a plurality of storage modules 104. FIGS. 10 and 11 each show a three-dimensional perspective view of a wedge-shaped vial storage module 104. FIG. 11 shows the storage module 104 including a plurality of specimen tubes 10, while FIG. 10 shows only a single tube 10, with a plurality of openings 105 sized to hold specimen tubes 10. In various embodiments, the wedge-shape of the storage module 104 allows for high-density placement of specimen tubes 10, when compared with conventional storage racks that include square or rectangular-shaped storage modules. That is, the wedge-shaped storage module 104 allows for storage of additional specimen tubes 10 in the storage rack 28, reducing space requirements in system 2. As shown, the storage module 104 can include at least one hook 110 on a radially outer wall 112, which allows a selector device (or a human user) to load and/or unload storage module(s) 104 from the support member 106 in rack 28. In some embodiments, each storage module 104 includes at least two hooks 110, which may increase stability in loading/unloading of storage modules 104 from rack 28.

In various embodiments, components described as being "coupled" to one another can be joined along one or more interfaces. In some embodiments, these interfaces can include junctions between distinct components, and in other cases, these interfaces can include a solidly and/or integrally formed interconnection. That is, in some cases, components that are "coupled" to one another can be simultaneously formed to define a single continuous member. However, in other embodiments, these coupled components can be formed as separate members and be subsequently joined through known processes (e.g., fastening, ultrasonic welding, bonding).

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A sample storage system comprising:
   a plurality of transport modules each having lateral sides;
   a storage module coupled to at least one of the transport modules on at least one of the lateral sides of the at least one transport module, the storage module including a multi-level storage rack having multiple columns of storage compartments configured for storing a plurality of specimen tubes or microtitre plates;
   a tube selector module coupled to an end of the at least one transport module for selecting at least one of the plurality of specimen tubes or microtitre plates; and
   an input/output (I/O) module coupled with the at least one transport module on one of the lateral sides of the at least one transport module,
   wherein the at least one transport module is configured to modularly couple with both another of the transport modules and at least one additional storage module for storing another plurality of specimen tubes or microtitre plates, the modular coupling of the at least one transport module to both the other transport module and the at least one additional storage module effecting dynamic expansion and/or contraction of the sample storage system.

2. The sample storage system of claim 1, wherein the I/O module further includes a storage rack.

3. The sample storage system of claim 1, wherein the transport modules include an access aperture at the end of the transport module coupled to the tube selector module.

4. The sample storage system of claim 1, further comprising the at least one additional storage module modularly coupled with the transport modules on another of the lateral sides of the transport modules.

5. The sample storage system of claim 1, wherein the transport modules include a multi-level transport system for transporting at least one of the plurality of specimen tubes or microtitre plates between distinct levels in the multi-level storage rack.

6. The sample storage system of claim 1, wherein the tube selector module includes a plurality of tube selectors.

7. The sample storage system of claim 1, wherein the transport modules include a service door providing access to the transport modules for service.

8. The sample storage system of claim 1, wherein the I/O module is configured to modularly attach and modularly detach from the transport modules on demand.

9. The sample storage system of claim 8, wherein the I/O module is configured to transport at least one of the plurality of specimen tubes or microtitre plates from the transport modules to an external system.

10. A sample storage system comprising:
a plurality of transport modules each having lateral sides;
a storage module coupled to at least one of the transport modules on at least one of the lateral sides of the at least one transport module, the storage module including a multi-level storage rack having multiple columns of storage compartments configured for storing a plurality of specimen tubes or microtitre plates;
a tube selector module coupled to an end of the at least one transport module for selecting at least one of the plurality of specimen tubes or microtitre plates; and
an input/output (I/O) module coupled with the at least one transport module on one of the lateral sides of the at least one transport module, the I/O module for at least one of inputting or outputting at least one of the plurality of specimen tubes or microtitre plates from the storage module via the at least one transport module,
wherein the at least one transport module is configured to modularly couple with both another of the transport modules and at least one additional storage module for storing another plurality of specimen tubes or microtitre plates, so as to effect dynamic expansion and/or contraction of the sample storage system.

11. The sample storage system of claim 10, wherein the I/O module further includes a storage rack.

12. The sample storage system of claim 10, further comprising the at least one additional storage module modularly coupled with the transport modules on another of the lateral sides of the transport modules.

13. The sample storage system of claim 10, wherein the transport module includes a multi-level transport system for transporting at least one of the plurality of specimen tubes or microtitre plates between distinct levels in the multi-level storage rack.

14. The sample storage system of claim 10, wherein the tube selector module includes a plurality of tube selectors.

15. The sample storage system of claim 10, wherein the transport modules include a service door providing access to the transport modules for service.

16. The sample storage system of claim 10, wherein the I/O module is configured to modularly attach and modularly detach from the transport modules on demand.

17. The sample storage system of claim 16, wherein the I/O module is configured to transport at least one of the plurality of specimen tubes or microtitre plates from the transport modules to an external system.

18. A sample storage system comprising:
a plurality of transport modules each having lateral sides and a transport rail system;
a plurality of storage modules coupled to the at least one transport module on at least one of the lateral sides of the at least one transport module, each of the plurality of storage modules including a multi-level storage rack having multiple columns of storage compartments configured for storing a plurality of specimen tubes or microtitre plates;
a tube selector module coupled to an end of the at least one transport module distinct from the at least one side, the tube selector module for selecting at least one of the plurality of specimen tubes or microtitre plates from the transport rail system; and
an input/output (I/O) module coupled with the at least one transport module on one of the lateral sides of the at least one transport module, the I/O module for at least one of inputting or outputting at least one of the plurality of specimen tubes or microtitre plates from the storage module via the at least one transport module,
wherein the at least one transport module is configured to modularly couple with both another of the transport modules and at least one additional storage module, for storing another plurality of specimen tubes or microtitre plates, so as to effect dynamic expansion and/or contraction of the sample storage system.

* * * * *